United States Patent
Gregg et al.

(10) Patent No.: US 9,603,532 B2
(45) Date of Patent: Mar. 28, 2017

(54) AUTOMATED IDENTIFICATION OF OCCLUSION LOCATION IN THE CUPRIT CORONARY ARTERY

(75) Inventors: Richard Gregg, Westford, MA (US); Sophia Huai Zhou, Briarcliff Manor, NY (US); Cheng-Hao Chien, Thousand Oaks, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 13/883,842

(22) PCT Filed: Nov. 28, 2011

(86) PCT No.: PCT/IB2011/055334
§ 371 (c)(1),
(2), (4) Date: May 7, 2013

(87) PCT Pub. No.: WO2012/073179
PCT Pub. Date: Jun. 7, 2012

(65) Prior Publication Data
US 2013/0237870 A1    Sep. 12, 2013

Related U.S. Application Data

(60) Provisional application No. 61/418,438, filed on Dec. 1, 2010.

(51) Int. Cl.
*A61B 5/02* (2006.01)
*A61B 5/04* (2006.01)
(Continued)

(52) U.S. Cl.
CPC ...... *A61B 5/02007* (2013.01); *A61B 5/04012* (2013.01); *A61B 5/0452* (2013.01); *A61B 5/0468* (2013.01)

(58) Field of Classification Search
CPC ... A61B 5/0402; A61B 5/04012; A61B 5/742; A61B 5/0452; A61B 5/7282; A61B 5/0006; A61B 5/02007; A61B 5/0468
(Continued)

(56) References Cited

U.S. PATENT DOCUMENTS 5,377,687 A   1/1995 Evans
6,217,525 B1  4/2001 Medema et al.
(Continued)

FOREIGN PATENT DOCUMENTS

JP   2002529873 A   9/2002
WO   0028893 A1    5/2000
(Continued)

OTHER PUBLICATIONS

Serafinovich et al: "Electrocardiographic Diagnosis for the Localization of Critical Occlusion in the Coronary Arteries"; GrGMU Journal 2008, 20 Page Document (Translation of article previously sent).
(Continued)

*Primary Examiner* — Michael Kahelin
*Assistant Examiner* — Minh Duc Pham

(57) ABSTRACT

A diagnostic ECG system analyzes lead traces for evidence of ST elevation in the lead signals. The pattern of ST elevation in leads having predetermined vantage points to the electrical activity of the heart and, in some instances, the presence of ST depression in certain other leads, identifies a specific coronary artery or branch as the culprit coronary artery for an acute ischemic event. ECG measurements which are associated with the identity of specific arterial occlusion locations are calculated and used to form a classifier of the probability of occlusion at different locations. The location identified as having the highest probability is indicated to a user as the most likely occlusion location.

14 Claims, 21 Drawing Sheets

(51) Int. Cl.
*A61B 5/0452* (2006.01)
*A61B 5/0468* (2006.01)

(58) Field of Classification Search
USPC .................................................. 600/508–509
See application file for complete search history.

(56) References Cited

U.S. PATENT DOCUMENTS

| | | | |
|---|---|---|---|
| 7,171,269 B1* | 1/2007 | Addison et al. .................. | 607/7 |
| 8,233,971 B2 | 7/2012 | Zhou et al. | |
| 2002/0107452 A1* | 8/2002 | Kwong .......................... | 600/509 |
| 2004/0138574 A1* | 7/2004 | Groenewegen .... | A61B 5/04023 600/509 |
| 2006/0206033 A1* | 9/2006 | Guerrero et al. ............. | 600/523 |
| 2006/0264770 A1* | 11/2006 | Wellens ............... | A61B 5/0452 600/509 |
| 2007/0219454 A1* | 9/2007 | Guzzetta ............. | A61B 5/0452 600/509 |

FOREIGN PATENT DOCUMENTS

| | | |
|---|---|---|
| WO | 2005046471 A1 | 5/2005 |
| WO | 2009019649 A1 | 2/2009 |
| WO | 2009077915 A1 | 6/2009 |
| WO | 2010099386 A1 | 9/2010 |

OTHER PUBLICATIONS

Almansori et al: "Electrocardiographic Identification of the Culprit Coronary Artery in Inferior Wall st Elevation Myocardial Infarction"; Can J. Cardiol. vol. 26, No. 6, Jun./Jul. 2010, pp. 293-296.

Fiol et al: "New Criteria Based on ST Changes in 12-Lead Surface ECG to Detect Proximal Versus Distal Right Coronary Artery Occlusion in a Case of Acute Inferoposterior Myocardial Infarction"; A.N.E., Oct. 2004, vol. 9, No. 4, pp. 383-388.

Hirai et al: "The Electrocardiogram in the Diagnosis of Acute Coronary Syndrome"; The 2nd Department of Internal Medicine, Toyama Medical and Pharmaceutical University, 2009, pp. 2561-2740.

Mori: "Regional Diagnosis of Cardiac Infarction by Electrocardiography"; Published Jul. 1986, pp. 1372-1378.

Tierala et al: "Predicting the Culprit Artery in Acute st-Elevation Myocardial Infarction and Introducing a New Algorithm to Predict Infarct-Related Artery in Inferior ST-Elevation Myocardial Infarction: Correlation With Coronary Anatomy in the Haamu Trial"; Science Direct, Journal of Electrocardiology 42, (2009), pp. 120-127.

Wang et al: "Electgrocardiographic Determination of Culprit Lesion Site in Patients With Acute Coronary Events"; Journal of Electrocardiology (009), pp. 46-51.

Serafinovich et al:"El;Ectrocardiographic Diagnostic of Localization of Critical Occlusion in the Coronary Artery"; GrGMU Journal 2008, pp. 121-126.

\* cited by examiner

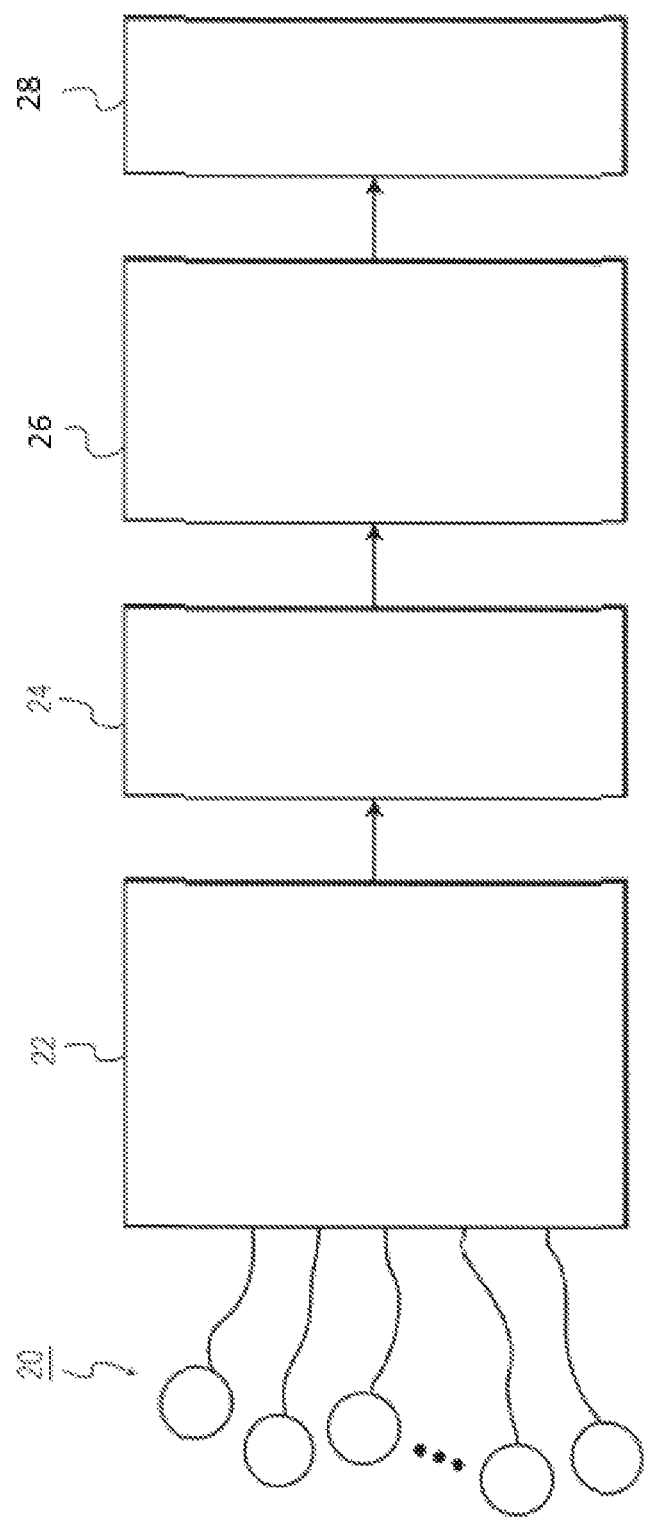

| | I | II | III | aVR | aVL | aVF | V1 | V2 | V3 | V4 | V5 | V6 |
|---|---|---|---|---|---|---|---|---|---|---|---|---|
| | 140 | 130 | 50 | -140 | 90 | 70 | 60 | 80 | 80 | 80 | 100 | 100 |
| | 88 | 132 | 64 | 128 | 92 | 120 | 44 | 96 | 124 | 116 | 116 | 160 |
| | 21 | 23 | 3 | -23 | 12 | 11 | 5 | 8 | 12 | 14 | 16 | 16 |
| | | | -50 | | | | -60 | | | | | |
| | | | 64 | | | | 80 | | | | | |
| | | | -3 | | | | -6 | | | | | |
| | -140 | | | -520 | -350 | | -1360 | -2910 | | -30 | | |
| | 36 | | | 84 | 52 | | 84 | 100 | | 16 | | |
| | 660 | 830 | 690 | | 850 | 760 | | | 20 | 600 | 780 | 800 |
| | 56 | 56 | 56 | | 40 | 56 | | | 12 | 28 | 56 | 76 |
| | | | -450 | -1070 | | -760 | | | -280 | -1130 | -240 | |
| | | 36 | 48 | | | 40 | | | 28 | 60 | 32 | |
| | | | | | | | | | 30 | | | |
| | | | | | | | | | 8 | | | |
| | | | | | | | | | -2440 | | | |
| | | | | | | | | | 64 | | | |
| | 76 | 44 | 44 | | 72 | 40 | | | 44 | 32 | 36 | 40 |
| | 800 | 1280 | 1760 | 520 | 1200 | 1520 | 1350 | 2910 | 2470 | 1730 | 1020 | 800 |
| | 92 | 92 | 104 | 84 | 92 | 96 | 84 | 100 | 112 | 104 | 88 | 76 |
| | 41 | 32 | -10 | -37 | 26 | 10 | -115 | -239 | -196 | -64 | 34 | 55 |
| | -60 | -50 | | 60 | -30 | -30 | 120 | 150 | 120 | | -60 | -60 |
| | -50 | -50 | | 40 | -20 | -20 | 180 | 250 | 170 | 10 | -50 | -50 |
| | -50 | -50 | -10 | 50 | -20 | -30 | 180 | 280 | 210 | 20 | -50 | -50 |
| | -50 | -50 | 10 | 10 | -20 | -10 | 250 | 350 | 200 | 20 | -60 | -30 |
| | 112 | 72 | 120 | 176 | 112 | 136 | 124 | 104 | 80 | 104 | 96 | 176 |
| | 3 | 1 | | -5 | 2 | 3 | 21 | 37 | 26 | 6 | | 2 |
| | STR | STR | STR | STR | STR | STR | STR | STR | STR | STR | STR | STR |
| | -50 | -50 | 200 | -100 | -120 | 180 | 350 | 520 | 460 | 90 | -70 | 110 |
| | 144 | 92 | 200 | 152 | 200 | 196 | 216 | 232 | 200 | 172 | 112 | 196 |
| | | 190 | | | | | | | | | 110 | |
| | | 176 | | | | | | | | | 188 | |
| | | 37 | | | | | | | | | 23 | |
| | 148 | 148 | 128 | 156 | 112 | 152 | 156 | 148 | 136 | 148 | 152 | 156 |
| | 12 | 16 | 16 | 20 | 12 | 16 | 24 | 76 | 20 | 16 | 20 | 20 |
| | 372 | 436 | 448 | 436 | 424 | 452 | 396 | 408 | 416 | 404 | 476 | 472 |
| | 1 | 1 | 1 | 1 | 1 | 1 | 1 | 1 | 1 | 1 | 1 | 1 |
| | MA.. | MA.. | NL | MA.. | NL | MA.. | NL | NL | NL | NL | MA.. | NL |
| | T | T | | T | | T | | | | | T | |

FIG. 9b

| I | aVR | V1 | V4 | V5R |
| --- | --- | --- | --- | --- |
| II | aVL | V2 | V5 | V4R |
| III | aVF | V3 | V6 | V8 |

FIG. 11c

AUTOMATED IDENTIFICATION OF OCCLUSION LOCATION IN THE CUPRIT CORONARY ARTERY

This invention relates to electrocardiograph systems and, in particular, to electrocardiograph systems which automatically identify the location of an occlusion in a culprit coronary artery which has caused an acute myocardial infarction.

Electrocardiography (ECG) is in widespread use to produce records derived from voltages produced by the heart on the surface of the human body. The records so produced are graphical in character and require expert interpretation and analysis to relate the resulting information to the heart condition of the patient. Historically, such records have been produced directly as visible graphic recordings from wired connections extending from the subject to the recording device. With advances in computer technology, it has become possible to produce such records in the form of digitally stored information for later replication and analysis.

An emergency clinical application where ECG records are critical is the analysis of symptoms of acute coronary disease, commonly referred to as heart attacks. Patients with acute coronary syndrome (ACS) such as chest pain or discomfort and shortness of breath are often diagnosed electrocardiographically. The ECG traces of a patient who has recently experienced a myocardial infarct can exhibit known characteristics such as elevation of the ST segment of a trace caused by complete obstruction, abnormal Q wave and/or T wave without ST elevation, or ST depression caused by partial obstruction. These conditions are characteristic of a stenosis in one of the two main coronary arteries, the right coronary artery (RCA) or left main (LM) coronary artery, or one of the two main branches of the LM, the left anterior descending (LAD) artery or the left circumflex (LCx) artery. An obstruction of one of these major conduits of blood to the myocardium should be cleared as quickly as possible to avert permanent damage to the heart muscle. Percutaneous coronary intervention (PCI) with a catheter device can open the infarct-related artery quickly to restore myocardial perfusion and is superior to thrombolytic therapy in many cases. This well established procedure provides a better long term outcome in terms of saving lives and improving quality of life.

Our international patent application publication no. WO2009019649A1 describes a method for the automated detection of the coronary artery is the cause of ST-elevation indicated myocardial infarction. The present invention further refines the method of our earlier patent application to automatically identify the location of the lesion within the culprit coronary artery. Not only can the pattern of ST-elevation and ST-depression be used to indicate the culprit or infarct-related coronary artery, the pattern can also be used to indicate whether the occlusion or stenosis is located in a proximal location or a more distal location. When the stenosis is in a proximal part of the coronary artery, close to the start of the coronary artery, the amount of heart muscle affected is much larger than if the stenosis were located further distal. Notation of a proximal occlusion is useful for risk stratification. If the coronary artery such as the left anterior descending (LAD) supplies a large portion of the blood supply to the left ventricle (LV) and if the clot is proximal, the risk to the patient is quite high. This is opposite the case where the coronary artery does not supply a large proportion of the LV blood flow, as in the case of obstruction of the left circumflex (LCx) when the clot is distal, in which case only a small proportion of the LV would be affected. So for a proximal occlusion of the LAD, the patient is in the highest risk category. In addition to risk being proportional to the amount of muscle downstream from the clot, the risk is higher for right ventricular infarcts. A proximal right coronary artery (RCA) occlusion involves the right ventricle and studies show higher mortality for RV infarct. Accordingly it is an object of the present invention to automatically identify the location of the obstruction to the culprit coronary artery so that the patient risk can be accurately assessed.

In accordance with the principles of the present invention, an automated analysis is described for devices with diagnostic ECG functionality such as electrocardiographs, defibrillators with diagnostic ECG functionality, bedside monitors with diagnostic ECG functionality and home ECG monitors with diagnostic ECG functionality to identify a culprit coronary artery. When a patient with ACS is undergoing an ECG test, this automated technique analyses the ECG signal for the presence of ST elevation, ST depression and deviations in other ECG measurements in specific ECG leads and automatically identifies the culprit artery. An embodiment of the present invention is capable of detecting an obstruction in one of the two main coronary arteries, the RCA and the LM, or one of the two main branches of the LM, the LAD and the LCx A plurality of ECG measurements which are useful in classifying the culprit coronary artery and are associated with occlusion locations are statistically analyzed. In a constructed embodiment a logical regression classifier is used to produce contour plots of probability surfaces for different occlusion locations such as proximal RCA, mid/distal RCA and LCx. ECG measurements are used to access points on the contour plots, and the value of the probability at a point on each plot is the probability of an occlusion location for that classification. The highest probability then determines the most likely site of the coronary occlusion.

In the drawings:

FIG. 5 is a block diagram of the major subsystems of a diagnostic ECG system.

FIGS. 9a and 9b illustrate the measurement of different parameters of an ECG trace.

FIG. 11c illustrates the standard representation of 12-lead signals in an ECG report and three additional leads which may be used for analysis in accordance with the present invention.

Figure 13A:
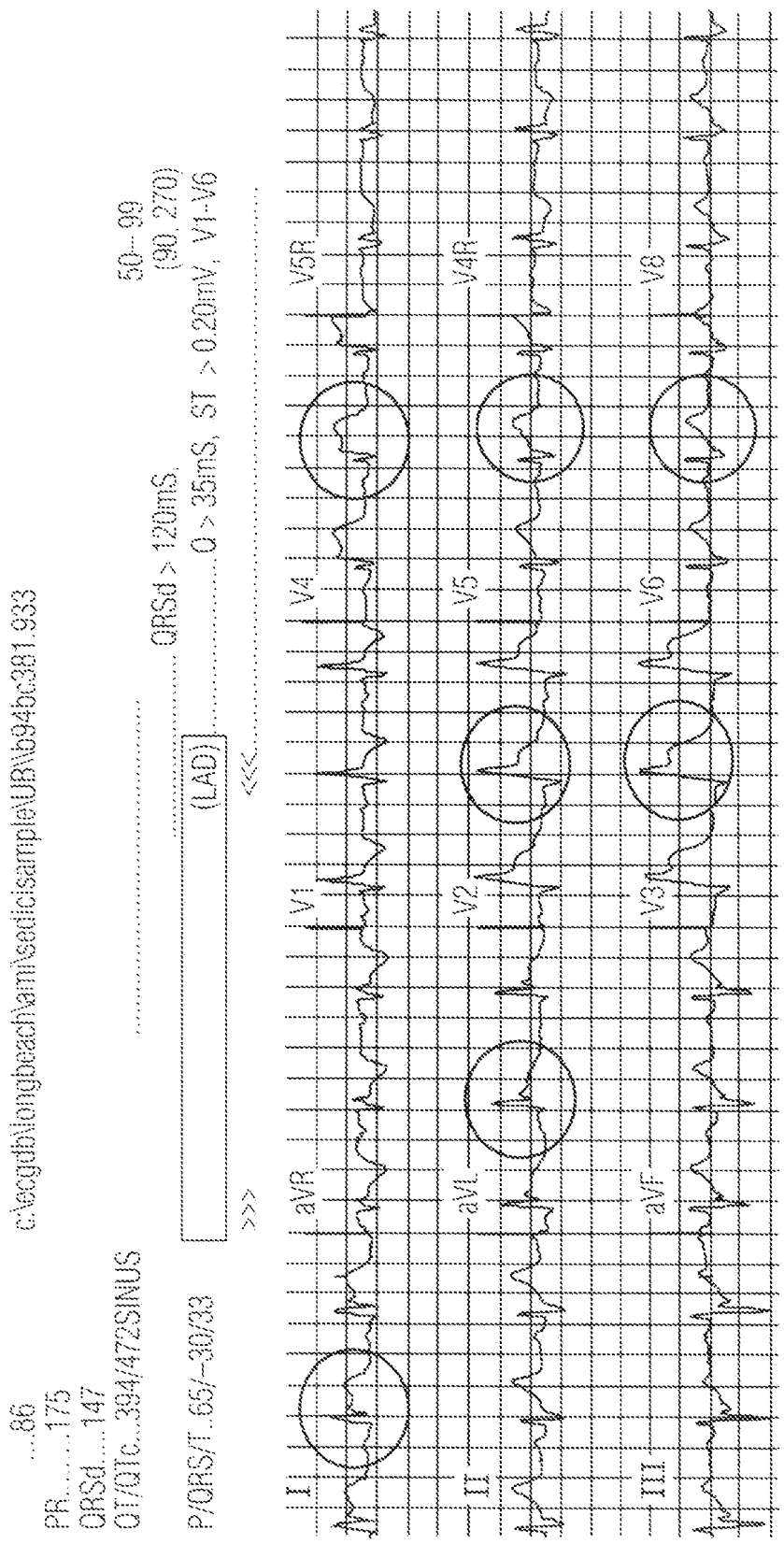
FIG. 13a illustrates an ECG report identifying the LAD as the culprit coronary artery in accordance with the principles of the present invention.
Figure 13C:
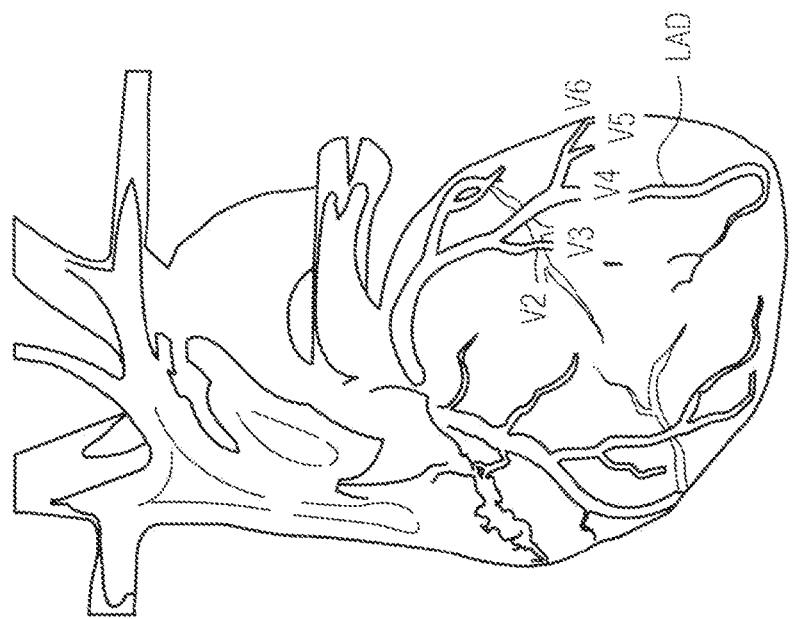
Figure 13B:
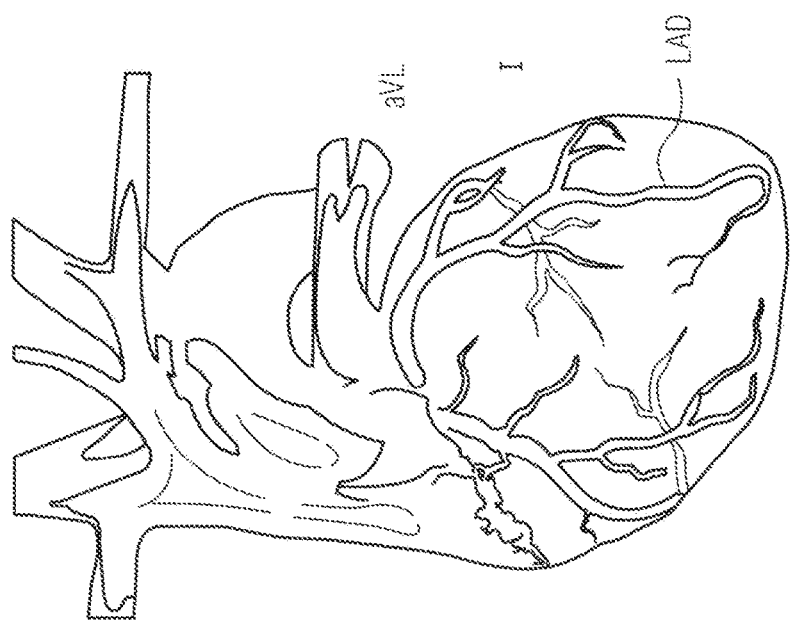

FIGS. 13b and 13c relate the elevated ST segments of the ECG report of FIG. 13a to specific regions of the heart in accordance with the principles of the present invention.

Figure 14A:
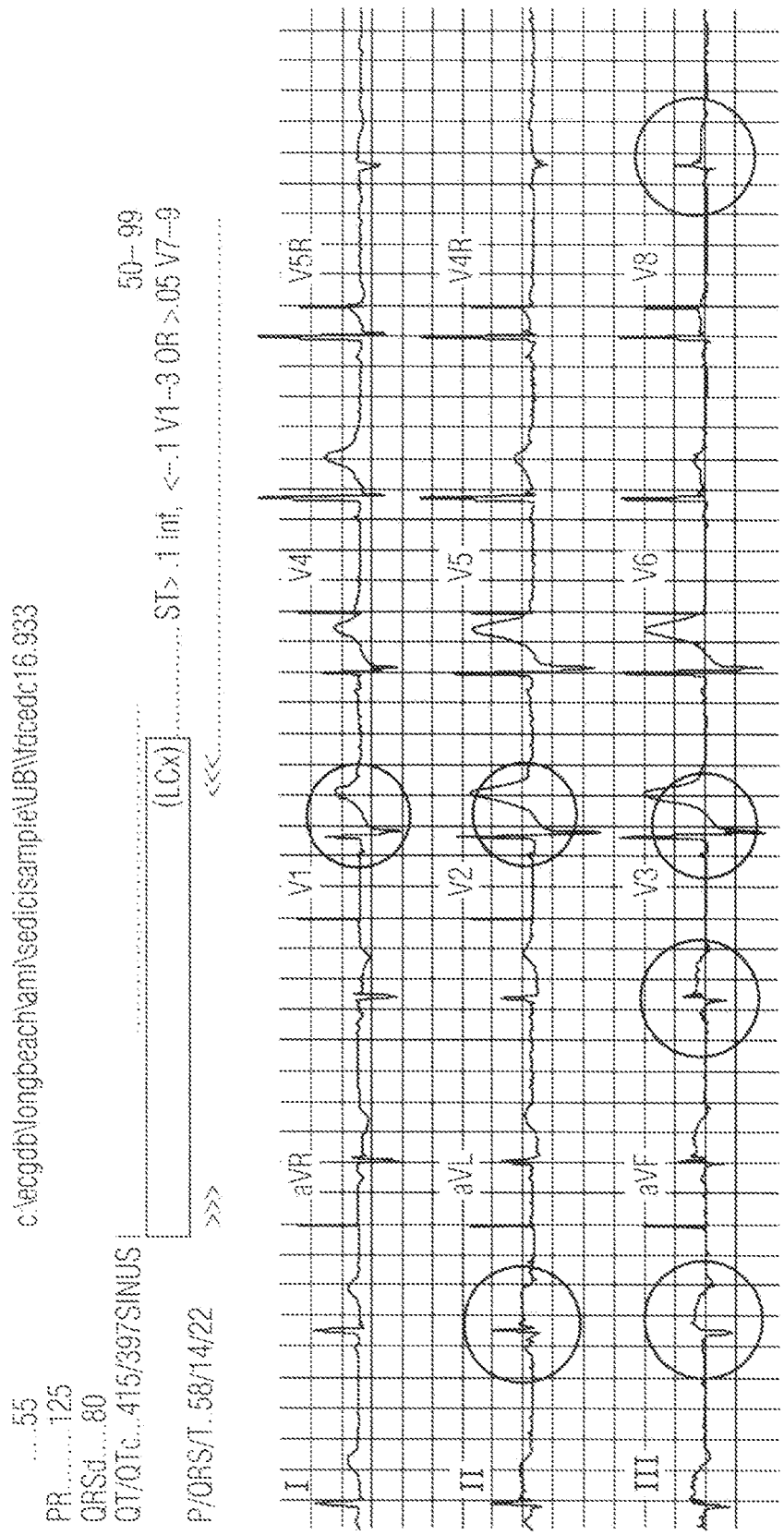

FIG. 14a illustrates an ECG report identifying the LCx as the culprit coronary artery in accordance with the principles of the present invention.

Figure 14C:
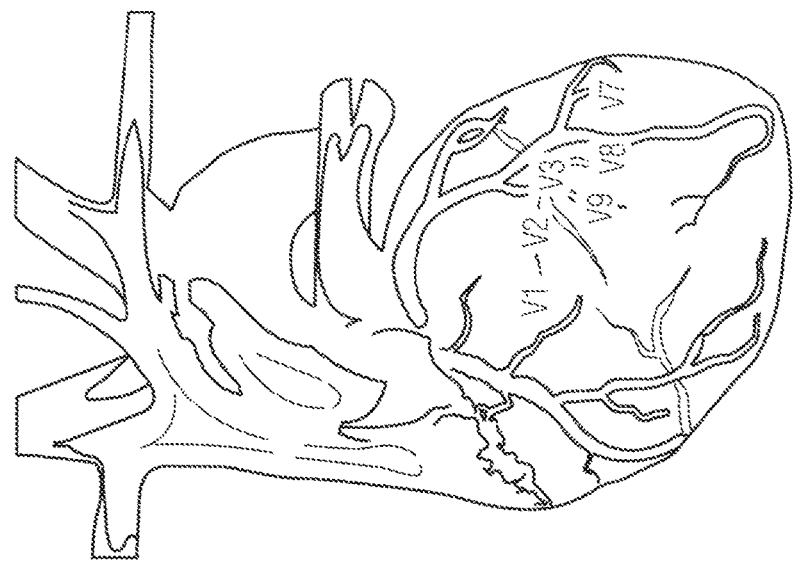
Figure 14B:
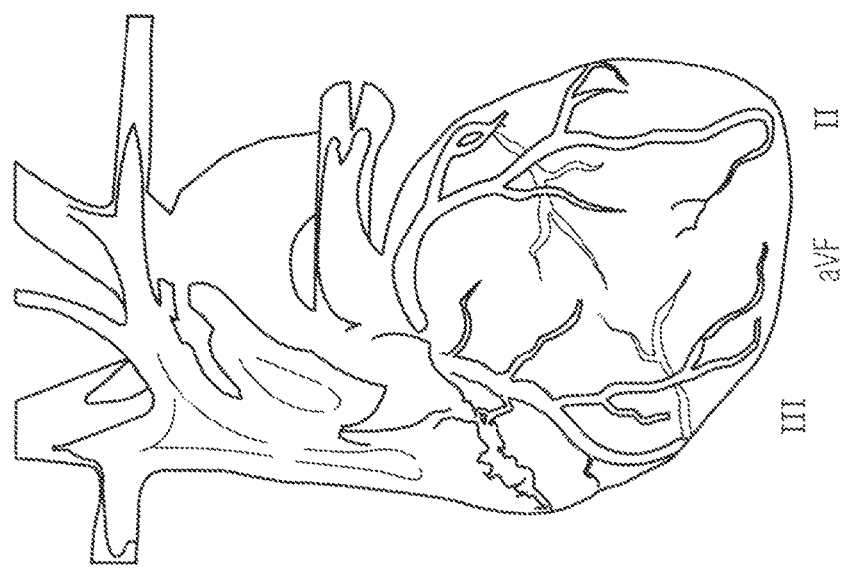

FIGS. 14b and 14c relate the elevated ST segments of the ECG report of FIG. 14a to specific regions of the heart in accordance with the principles of the present invention.

Figure 15A:
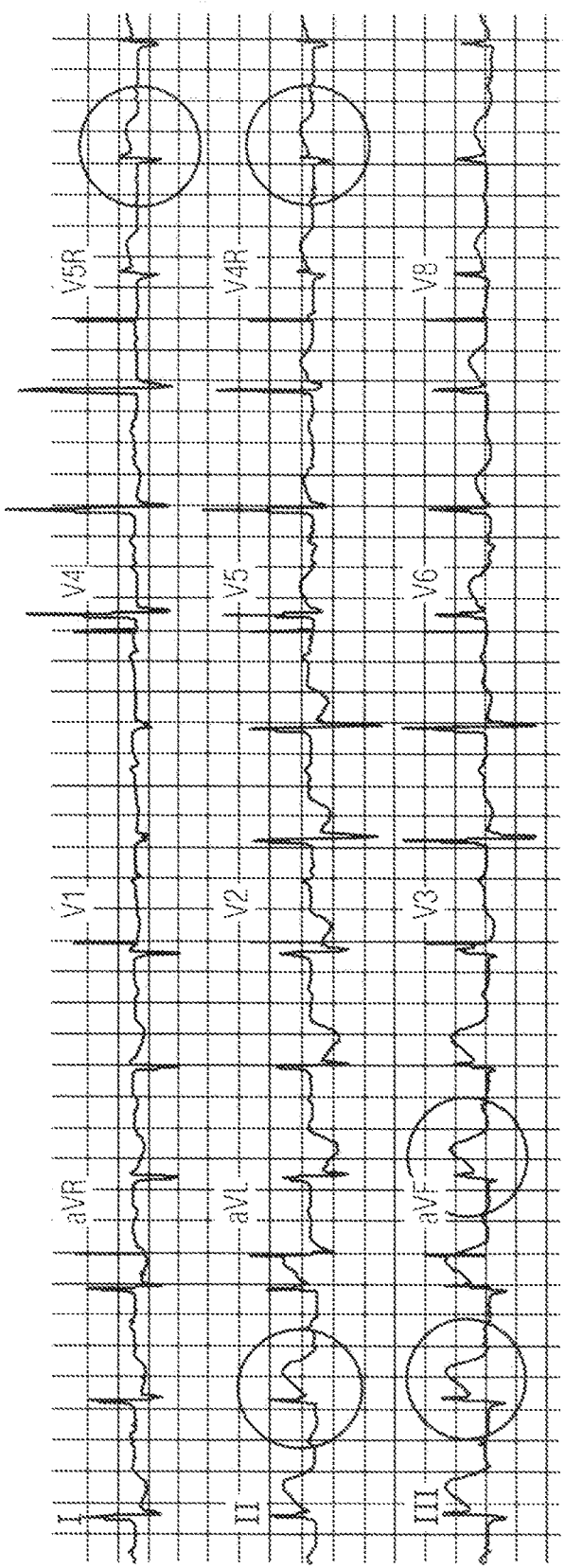

FIG. 15a illustrates an ECG report identifying the RCA as the culprit coronary artery in accordance with the principles of the present invention.

Figure 15C:
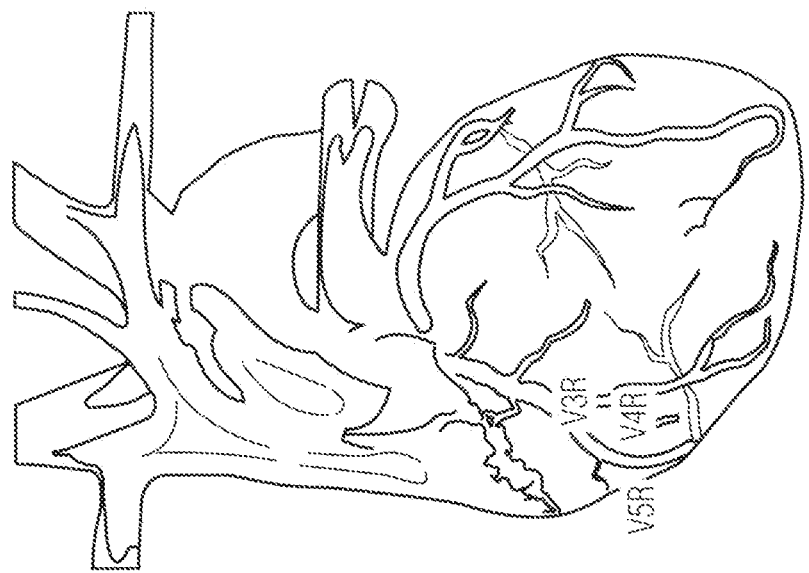
Figure 15B:
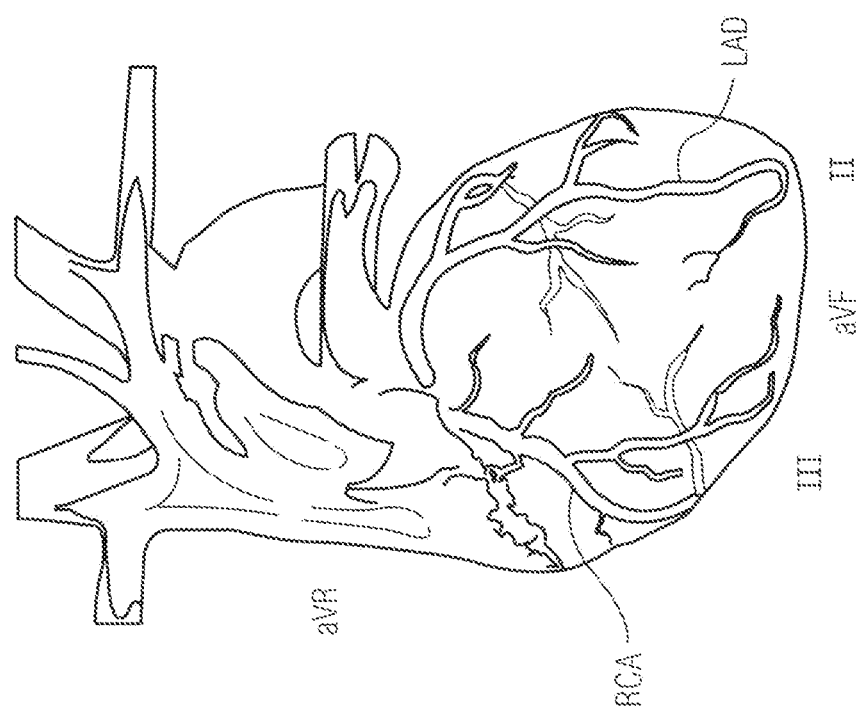

FIGS. 15b and 15c relate the elevated ST segments of the ECG report of FIG. 15a to specific regions of the heart in accordance with the principles of the present invention.

Figure 16:
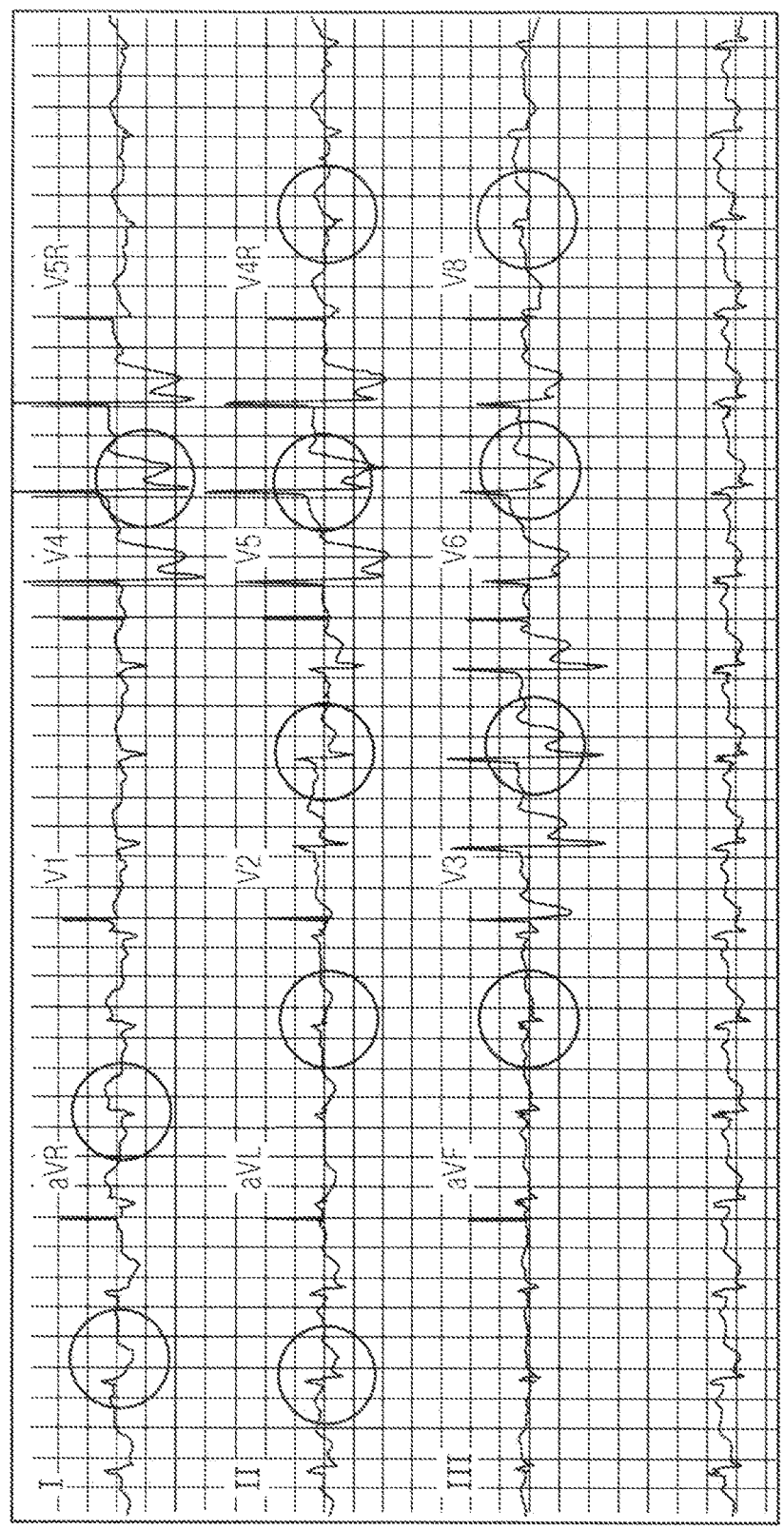

FIG. 16 illustrates an ECG report identifying the left main coronary artery as the culprit coronary artery in accordance with the principles of the present invention.

Figures 17A, 17B, 17C:
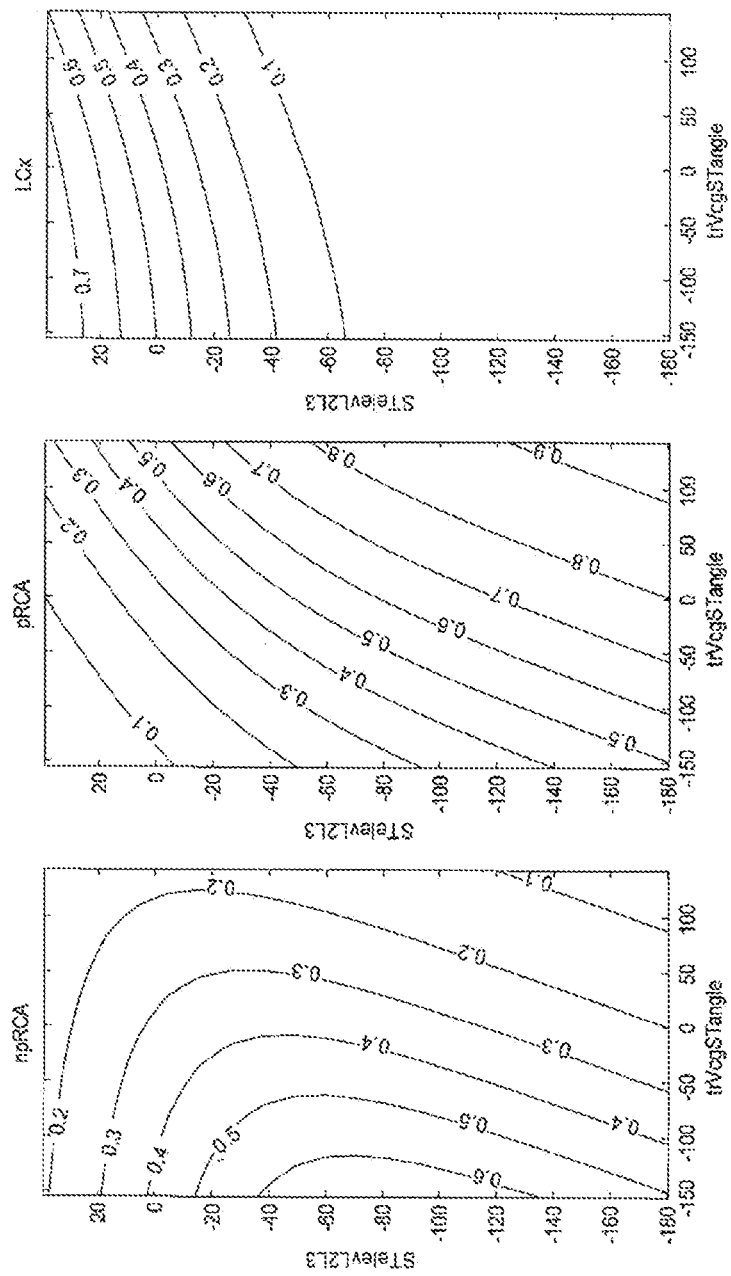

FIGS. 17a, 17b and 17c illustrate contour plots of probability surfaces for a logical regression classifier for the classification of ECG measurements in STEMI indicating occlusion of the proximal RCA, mid/distal RCA, and LCx arterial locations.

Figure 1:
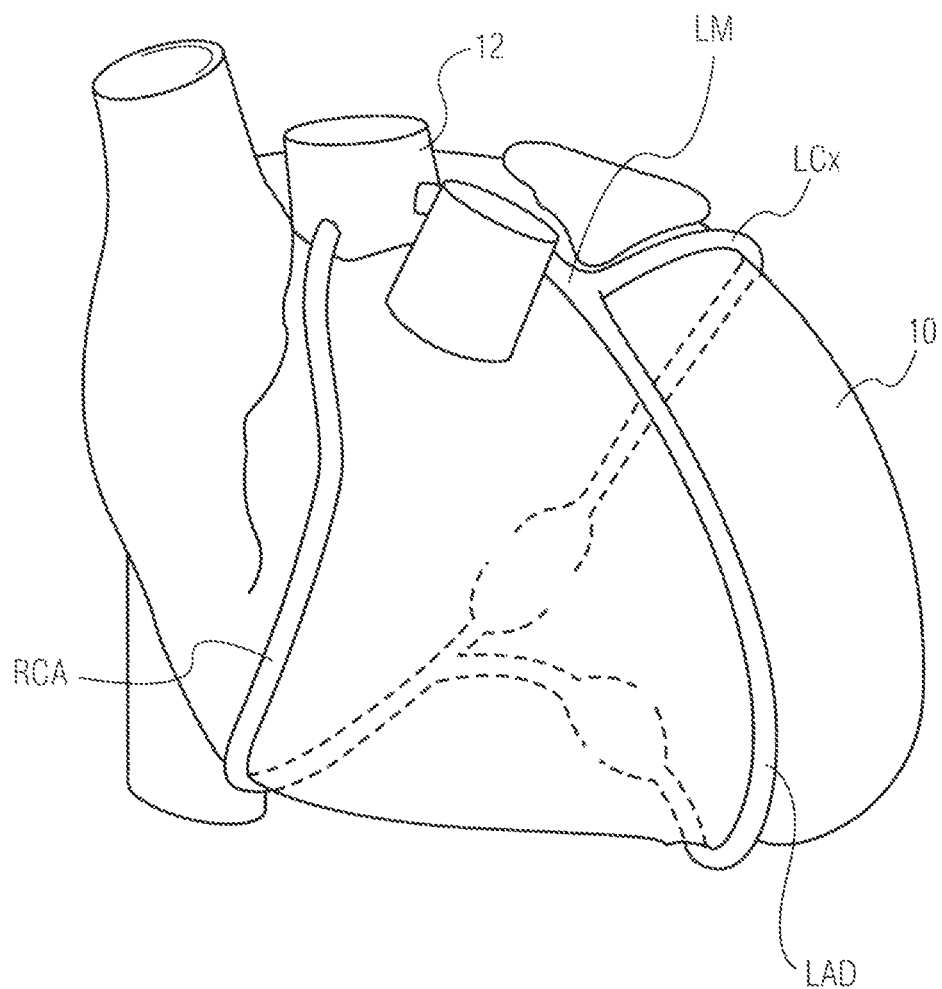
FIG. 1 is a highly schematic illustration of a heart and its major coronary arteries.
Figure 2:
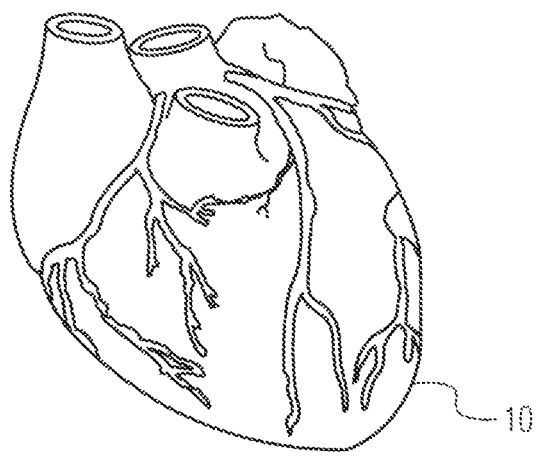
FIG. 2 is an anatomical illustration of the heart and coronary arteries.
Figure 3:
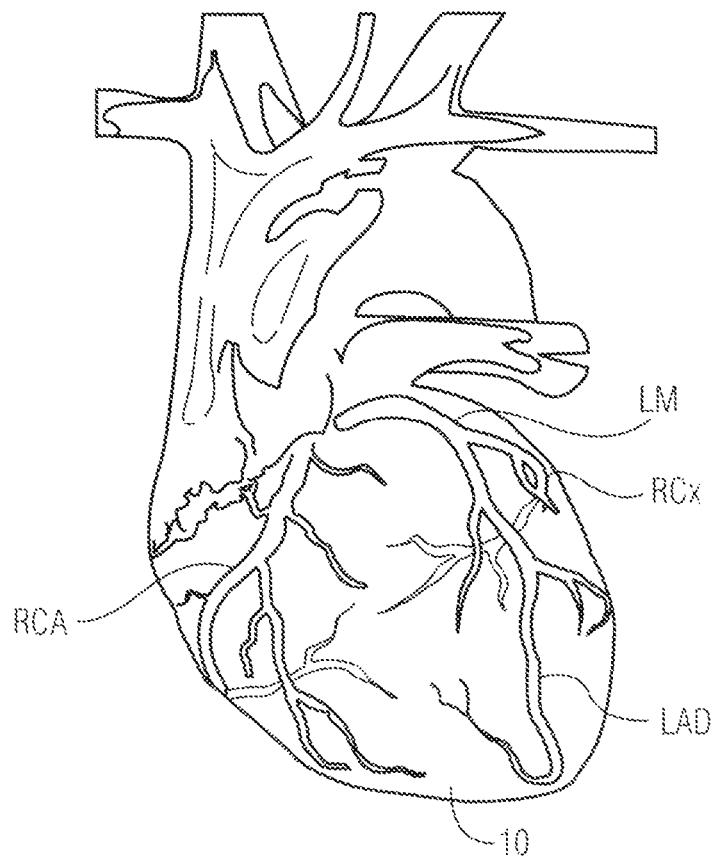
FIG. 3 is a translucent anatomical illustration of the heart, showing the coronary arteries wrapping around the heart.

FIGS. 1-3 are various views of the heart showing the locations of the coronary arteries which, when obstructed, will cause significant damage to the heart. FIG. 1 is a highly schematic view which shows the right coronary artery (RCA) descending along the right side of the heart 10 from the aorta 12. Also descending from the aorta along the left side of the heart is the left main (LM) coronary artery, which quickly branches to form the left anterior descending (LAD) artery on the front (anterior) of the heart and the left circumflex (LCx) artery which wraps around the back (posterior) of the heart. All three major vessels are seen to ultimately wrap around the heart 10 in characteristic tortuous paths to provide a constant supply of fresh blood to the myocardium.

FIG. 2 shows the same arteries and branches from the anterior side of the heart 10 in a more anatomically correct depiction of the heart. In FIG. 3 the heart 10 is depicted as a translucent orb so that the tortuous paths of the coronary arteries on both the anterior and posterior sides of the heart can be readily visualized.

Figure 4A:
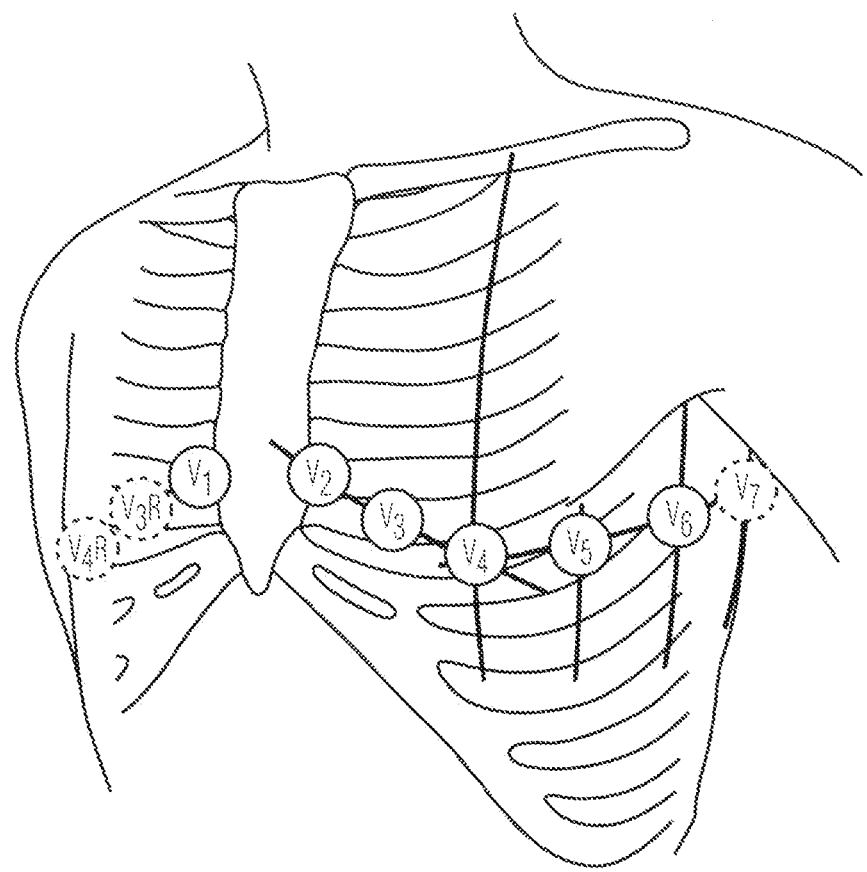
FIGS. 4a and 4b show standard electrode placement for an ECG exam.

It is an object of the present invention to be able to automatically identify which of these coronary arteries and branches is obstructed from an analysis of the traces of a standard or non-standard ECG exam. Correct interpretation of an ECG requires a great deal of experience since it involves familiarity with a wide range of patterns in the tracings of the various leads. Any ECG which uses an unconventional system of leads necessarily detracts from the body of experience that has been developed in the interpretations of conventional ECGs, and may therefore be considered generally undesirable. The tracings generated would be understandable only by a relative few who were familiar with the unconventional system. Thus it is significant that the present invention can be implemented in a standard ECG exam with conventional electrode placement. FIG. 4a shows the placement of six electrodes, V1-V6, which are located on the torso of the patient for a conventional 12-lead ECG exam with ten lead electrodes. Each electrode acts in combination with one or more other electrodes to detect voltages produced by depolarization and repolarization of individual heart muscle cells. The detected voltages are combined and processed to produce twelve tracings of time varying voltages. The tracings so produced are as follows:

| Lead | Voltage |
| --- | --- |
| I | VL − VR |
| II | VF − VR |
| III | VF − VL |
| aVR | VR − (VL + VF)/2 |
| aVL | VL − (VR + VF)/2 |
| aVF | VF − (VL + VR)/2 |
| V1 | V1 − (VR + VL + VF)/3 |
| V2 | V2 − (VR + VL + VF)/3 |
| V3 | V3 − (VR + VL + VF)/3 |
| V4 | V4 − (VR + VL + VF)/3 |
| V5 | V5 − (VR + VL + VF)/3 |
| V6 | V6 − (VR + VL + VF)/3 | where, in the standard, most widely used system for making short term electrocardiographic recordings of supine subjects, the potentials indicated above, and their associated electrode positions, are:

VL potential of an electrode on the left arm;

VR potential of an electrode on the right arm;

VF potential of an electrode on the left leg;

V1 potential of an electrode on the front chest, right of sternum in the 4th rib interspace;

V2 potential of an electrode on the front chest, left of sternum in the 4th rib interspace;

V4 potential of an electrode at the left mid-clavicular line in the 5th rib interspace;

V3 potential of an electrode midway between the V2 and V4 electrodes;

V6 potential of an electrode at the left mid-axillary line in the 5th rib interspace;

V5 potential of an electrode midway between the V4 and V6 electrodes;

G (not indicated above) is a ground or reference potential with respect to which potentials VL, VR, VF, and V1 through V6 are measured. Typically, though not necessarily, the ground or reference electrode is positioned on the right leg.

Figure 4B:
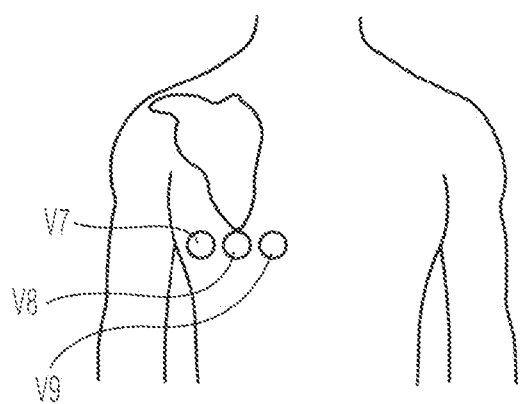

The present invention is suitable for use with conventional 12-lead EGG systems as well as with 13-, 14-, 15-, 16-, 17-, or 18-lead systems or greater, including 56- and 128-lead body surface mapping systems. Three-lead (EASI and other), 5-, and 8-lead systems can also be used to derive 12 leads, with reduced accuracy as is known in the art. See, for example, U.S. Pat. No. 5,377,687 (Evans et al.) and U.S. Pat. No. 6,217,525 (Medema et al.) In sum, an implementation of the present invention can employ any number of leads and electrodes. FIGS. 4a and 4b show some of the electrodes used by higher order lead systems. The V7, V8, and V9 electrodes are seen to continue to wrap around the torso from the V6 electrode. The V3R, V4R, V5R and additional electrodes proceed around the right side of the body, mirroring the positions of the V3, V4, V5 and other electrodes on the left side of the body.

FIG. 5 illustrates in block diagram form a diagnostic ECG system suitable for use with the present invention. A plurality of electrodes 20 are provided for attaching to the skin of a patient. Usually the electrodes are disposable conductors with a conductive adhesive gel surface that sticks to the skin. Each conductor has a snap or clip that snaps or clips onto an electrode wire of the ECG system. The electrodes 20 are coupled to an ECG acquisition module 22 that preconditions the signals received by the electrodes. The electrode signals are coupled to an ECG processing module 26, generally by means of an electrical isolation arrangement 24 that protects the patient from shock hazards and also protects the ECG system when the patient is undergoing defibrillation, for instance. Optical isolators are generally used for electrical isolation. The processed ECG information is then displayed on an image display or printed in an ECG report by an output device 28.

Figure 6:
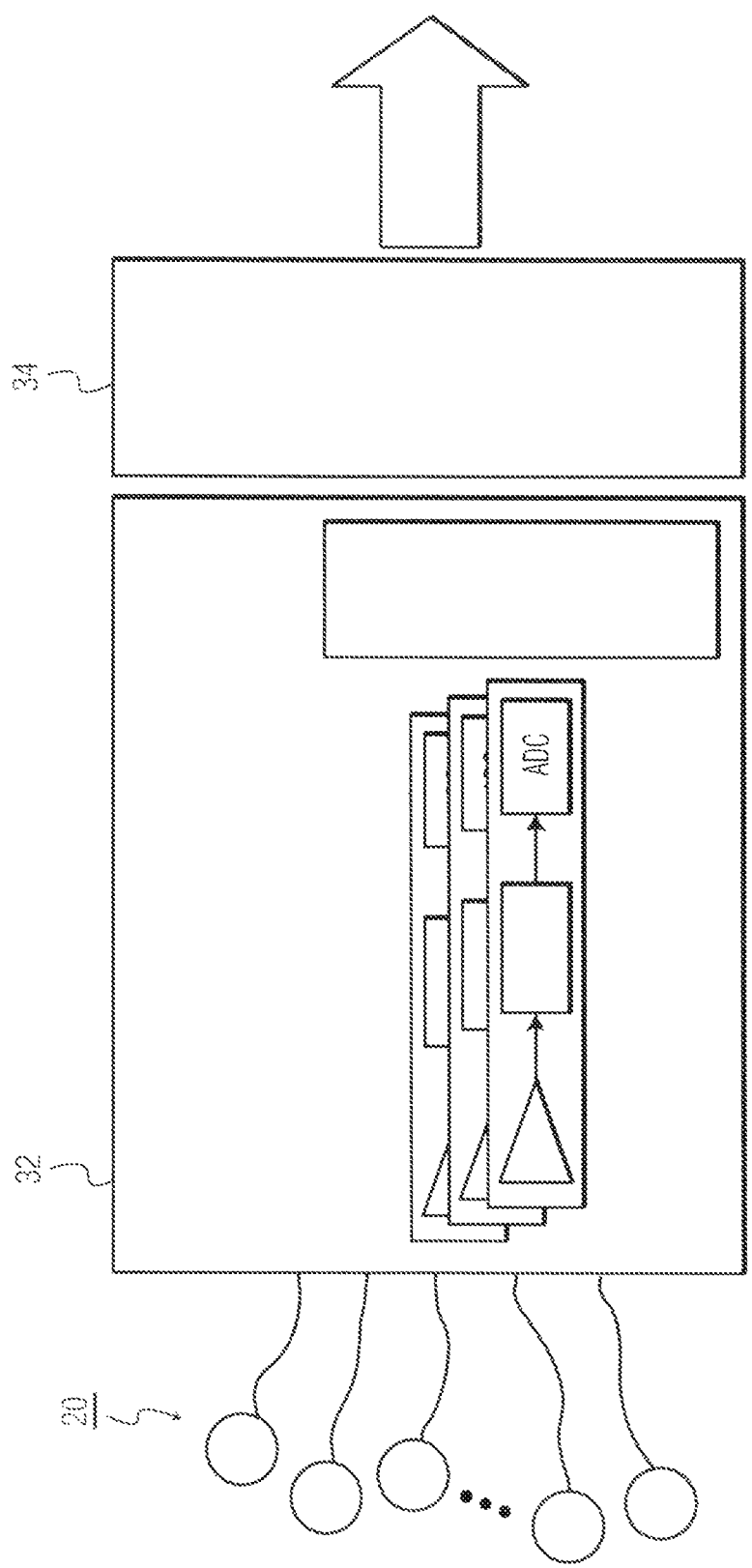
FIG. 6 is a block diagram of the front end of an ECG system.

FIG. 6 shows the acquisition module 22 in greater detail. The electrode signals, which are usually just a few millivolts in amplitude, are amplified by amplifiers which also usually have high voltage protection from defibrillation pulses. The amplified signals are conditioned as by filtering and then converted to digitally sampled signals by analog to digital converters. The signals are then formatted by differentially combining various electrode signals to derive lead signals in combinations such as those given above for a 12-lead system. The digital lead signals are forwarded for ECG processing under control of CPU 34. Much of the specialized electronics of the acquisition module is often implemented in the form of an application-specific integrated circuit (ASIC).

Figure 7:
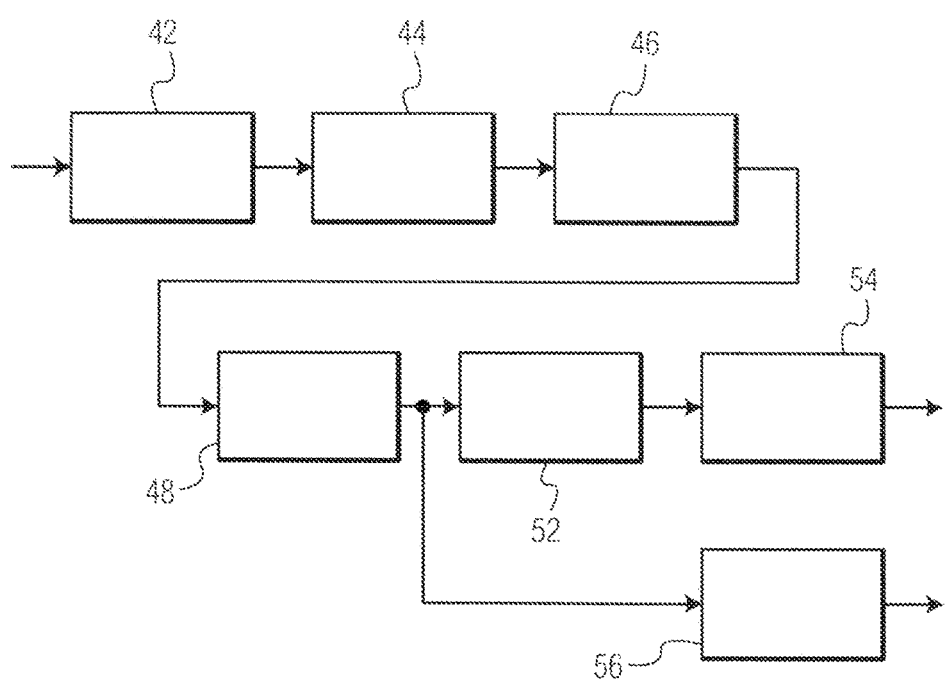
FIG. 7 is a block diagram of the processing module of a typical diagnostic ECG system.
Figure 8:
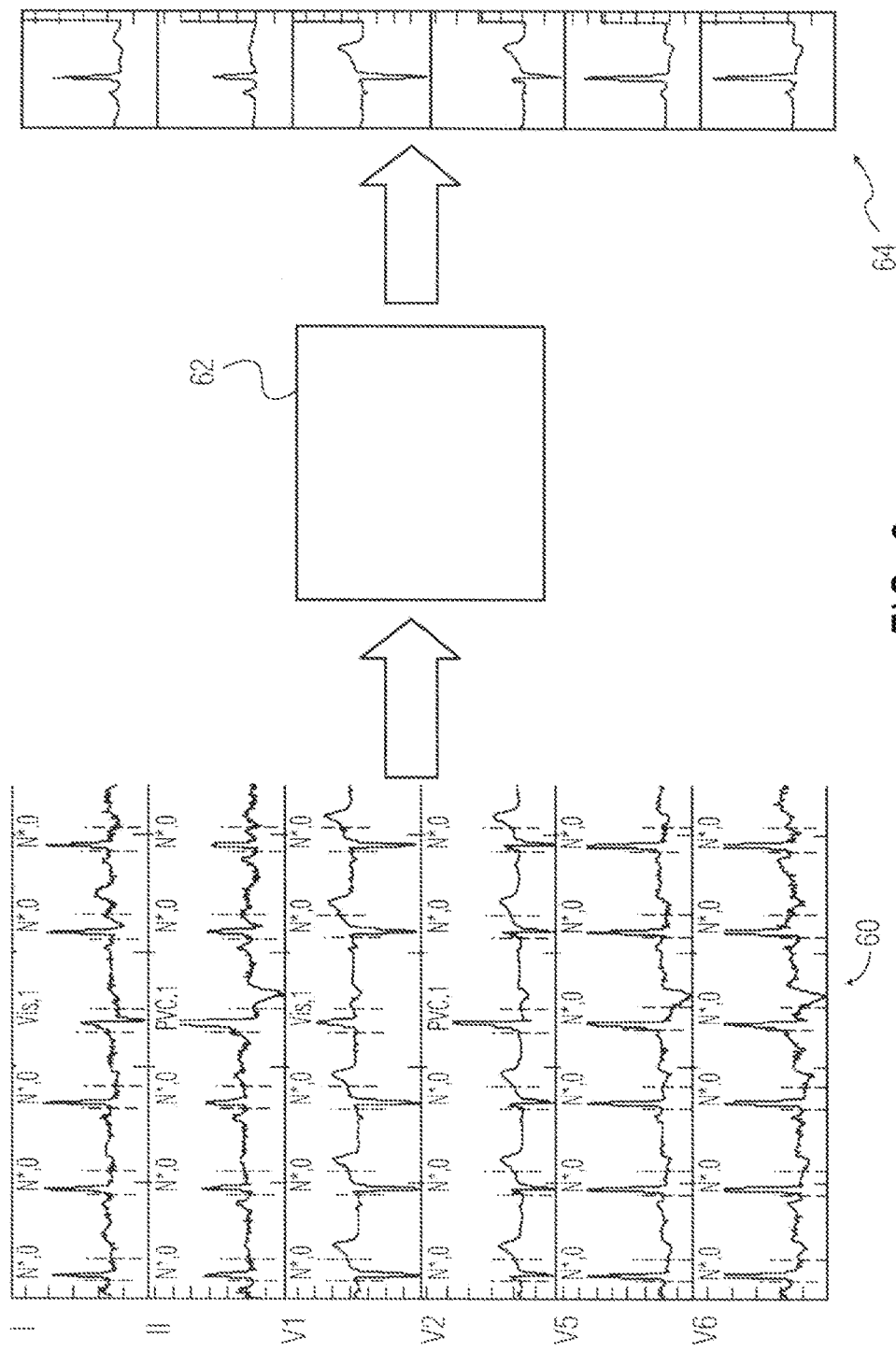
FIG. 8 illustrates the processing of ECG trace data to provide information about the heartbeat and its rhythm.
Figure 9A:
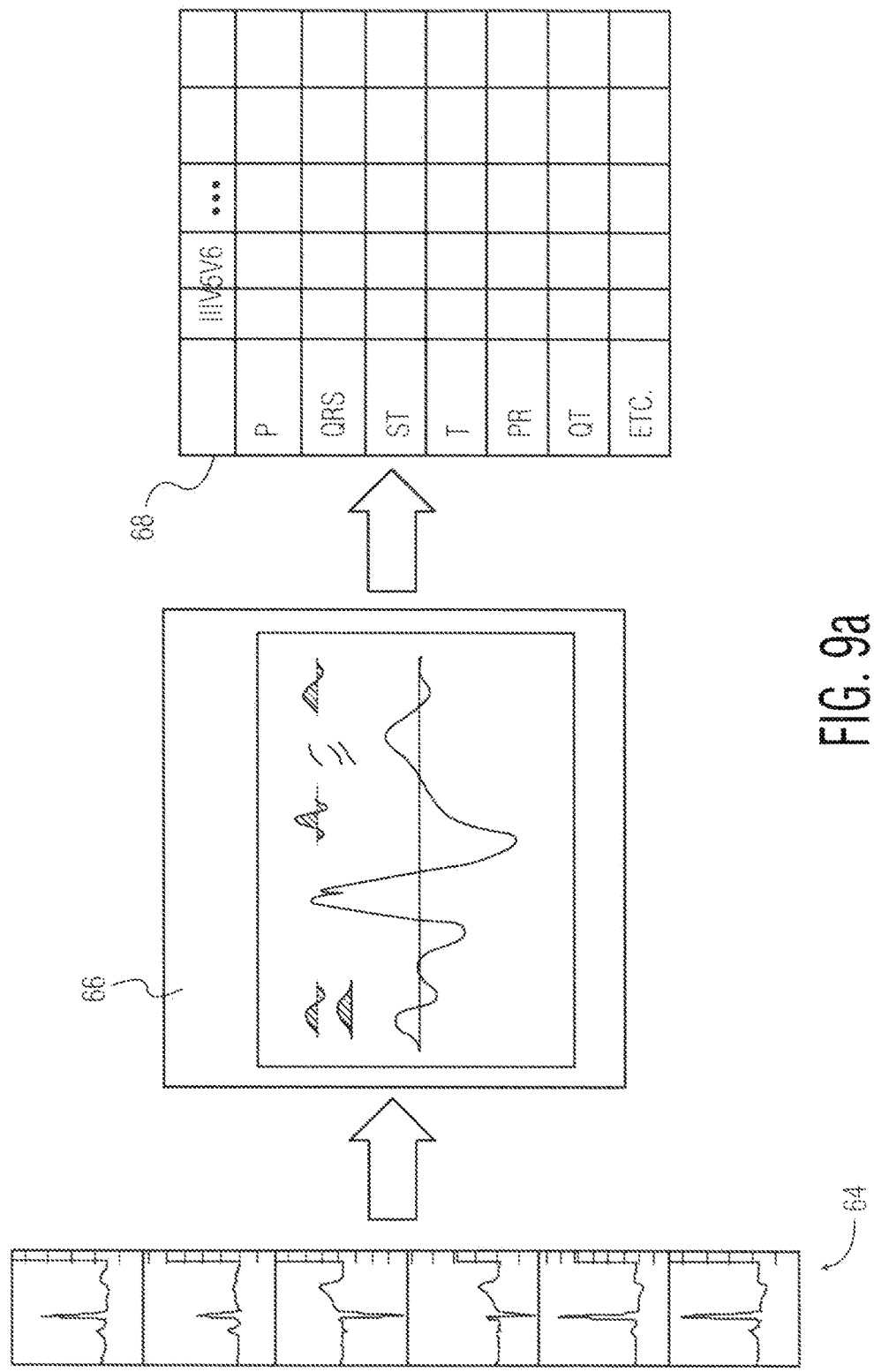
Figure 12A:
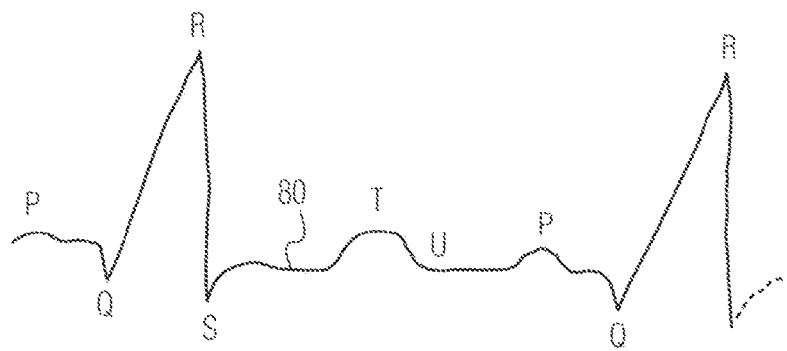
FIG. 12a illustrates the segments of a normal ECG signal.

FIG. 7 is a block diagram of the analysis portion of a typical diagnostic ECG system. A pace pulse detector 42 identifies and sets aside electrical spikes and other electrical abnormalities produced by a pacemaker for patients who are wearing one. A QRS detector 44 detects the dominant pulse of the electrical traces. FIG. 12a illustrates a typical normal ECG trace, where it is seen that the Q-R-S segments delineate the major electrical pulse of the trace, which is the pulse that stimulates a contraction of the left ventricle. Delineation of the QRS complex forms the basis for detecting the lesser perturbations of the trace, which is performed by the waveform segmenter 46. The waveform segmenter delineates the full sequence of trace segments including the P wave and the Q to U segments of the ECG trace. With each waveform now fully delineated, a beat classifier 48 compares each new beat with previous beats and classifies beats as normal (regular) for the individual or abnormal (irregular). The classification of the beats enables an average beat analyzer 52 to define the characteristics of a normal heartbeat and the amplitudes and segment durations of an average beat are measured at 54. The beat classifications are used to determine the heart rhythm at 56. FIGS. 8, 9a and 9b are functional illustrations of this ECG trace processing. At the left side of FIG. 8 is a series 60 of ECG traces from leads I, II, V1, V2, V5 and V6. The beat classifier 48 compares the various beat characteristics and has classified some of the beats as normal (N*,0). For example, all of the beats from leads V5 and V6 have been classified as normal. The other four leads contain a beat exhibiting the characteristics of premature ventricular contraction (PVC,1). At 62 the ECG system aggregates the characteristics of the normal beats, excludes characteristics of the abnormal beats, aligns the beats in time and averages them to produce an average beat. The traces at 64 illustrate the traces of an average beat for the six leads shown in this example. In FIG. 9a the average beat traces 64 of the six leads are measured for various characteristics shown at 66, such as the amplitudes and durations of the Q wave, the R wave, and the T wave and inter-wave intervals such as QRS and QT. The measurements are illustrated as recorded in a measurement table 68 for the six leads of this example. An example of a complete measurement table for a 12-lead system is shown in FIG. 9b.

Figure 10:
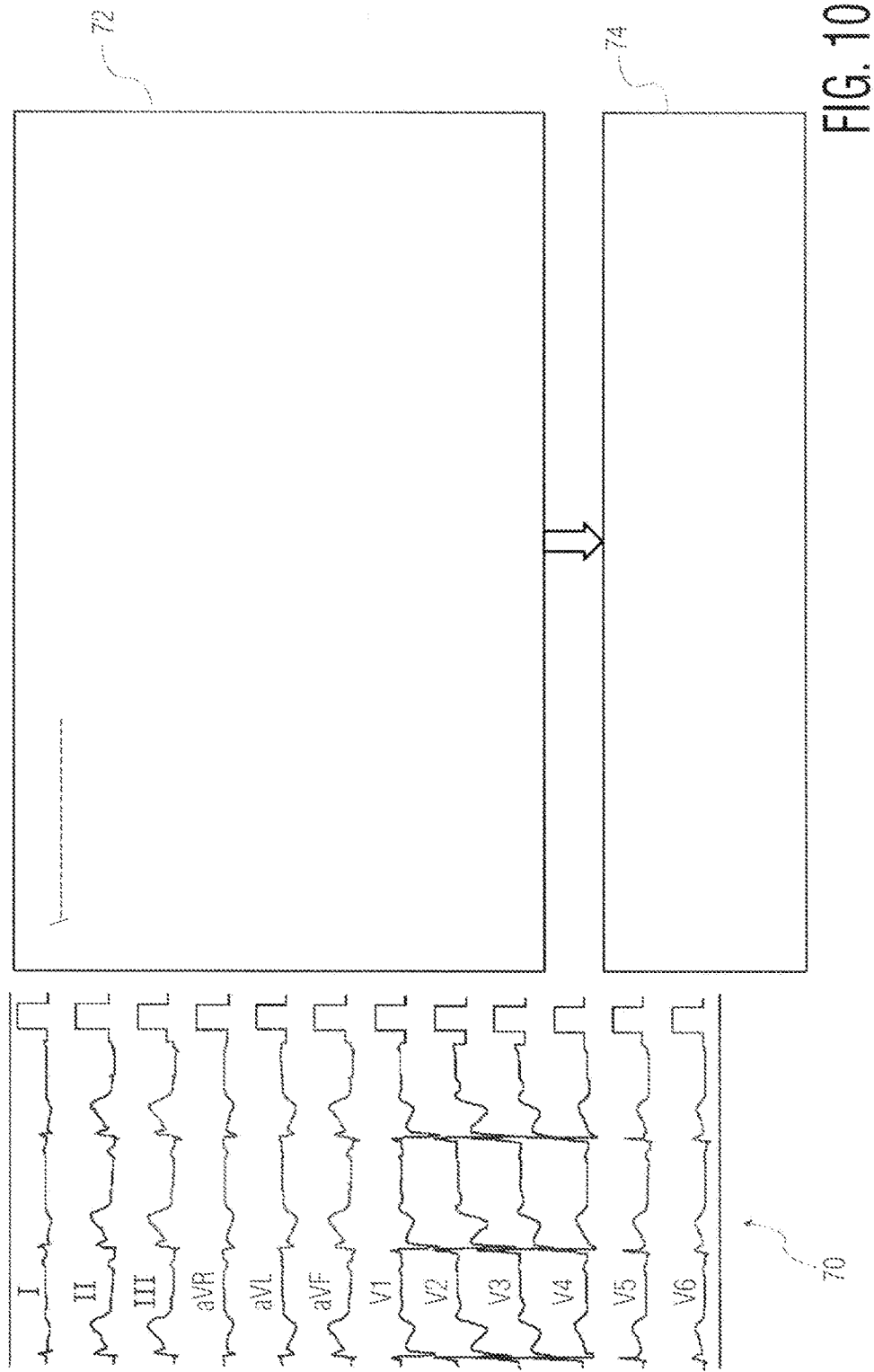
FIG. 10 illustrates a typical ECG report.

The ECG waves and their measurements can be sent to an offline workstation with a report generation package for the production of a report on the patient's ECG waveforms. However most diagnostic ECG systems such as the Philips Pagewriter® line of cardiographs and the Philips TraceMaster® ECG management system have onboard ECG reporting packages. FIG. 10 illustrates the type of reports that can be produced by these systems. From the characteristics of the waveforms of the twelve leads shown at 70 and the measurements of FIG. 9b, the clinician can program the reporting software to identify and logically combine, include, or exclude various characteristics in ways that clinically define certain cardiac symptoms. A typical program of this type is shown at 72 in FIG. 10 and will lead to an ECG report for the treating cardiologist as shown at 74. For a patient who has suffered an acute myocardial infarct the report will usually indicate the existence of acute myocardial ischemia within the heart and, at times, some area localization of the region of the heart and the size of the area impacted by the infarct. However, for an interventional cardiologist waiting with catheter in hand to clear the obstruction, more information is needed. The cardiologist wants to know which major coronary artery and which branch of the coronaries has been blocked, so that the cardiologist can immediately proceed to catheterize the blocked artery or branch and return blood perfusion to the affected region of the heart.

In accordance with the principles of the present invention, the present inventors have studied the statistical analyses of ECG databases and their relationship to different coronary artery anatomies and have developed an automated technique to identify the culprit artery of an acute ischemic event and the most likely location of the occlusion. The inventive technique can identify one of the two main coronary arteries, the RC and the LM, or one of the two main branches of the LM, the LDA or the LCx, as the culprit artery. The cardiologist is then informed of the identity of the culprit artery and the occlusion location as by identifying them in the ECG report, visually on a screen, on a display of ECG traces, audibly, or by other output means. The present inventors have recognized that ST deviations and other ECG measurements (e.g., amplitudes and durations of the Q wave, R wave, T wave and inter-wave intervals such as QRS and QT) in the resting ECG, in situations with ST segment elevation and without ST segment elevation and acute cardiac ischemia have different patterns if obstructions occur in different coronary arteries and in different levels of the artery. Considering that the coronary anatomy has certain patterns and deviations, these ST deviations are closely associated with the patient's coronary artery anatomy. The inventive technique is able to examine ST deviations and other measurements of standard ECG lead configurations and their classification rules to conclude that a specific coronary artery or branch is the source of an acute ischemic event.

For instance, if the LAD is occluded the flow of blood to the anterior wall of the heart will be reduced. In this situation some of ECG leads V2, V3, V4, V5 facing the anterior wall will show ST elevation. Correspondingly, the ECG leads facing the opposite wall of the heart will show ST depression. By using this principle, the culprit coronary artery or branch supplying the acutely infarcted region of the heart wall can be identified.

Figure 11B:
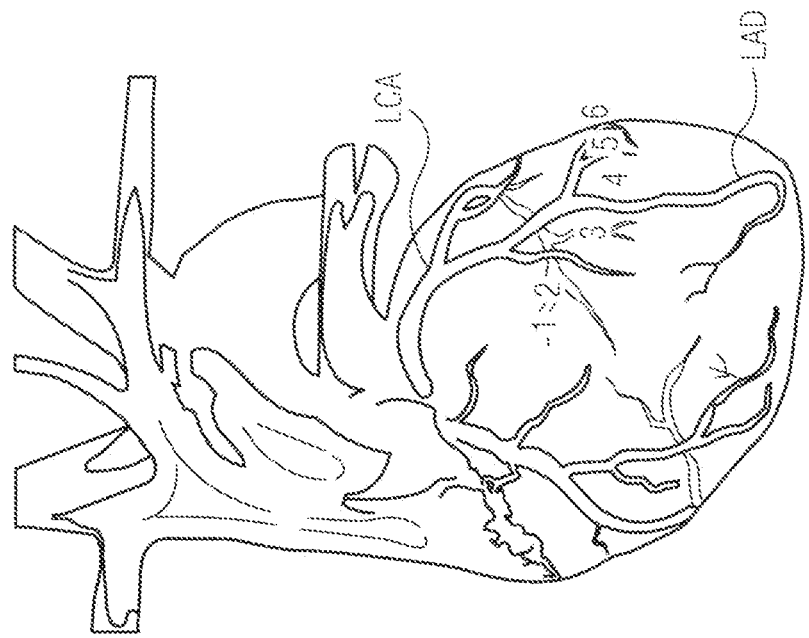
FIGS. 11a and 11b illustrate the relationship between the leads of a 12-lead system and the anatomy of the coronary arteries.
Figure 11A:
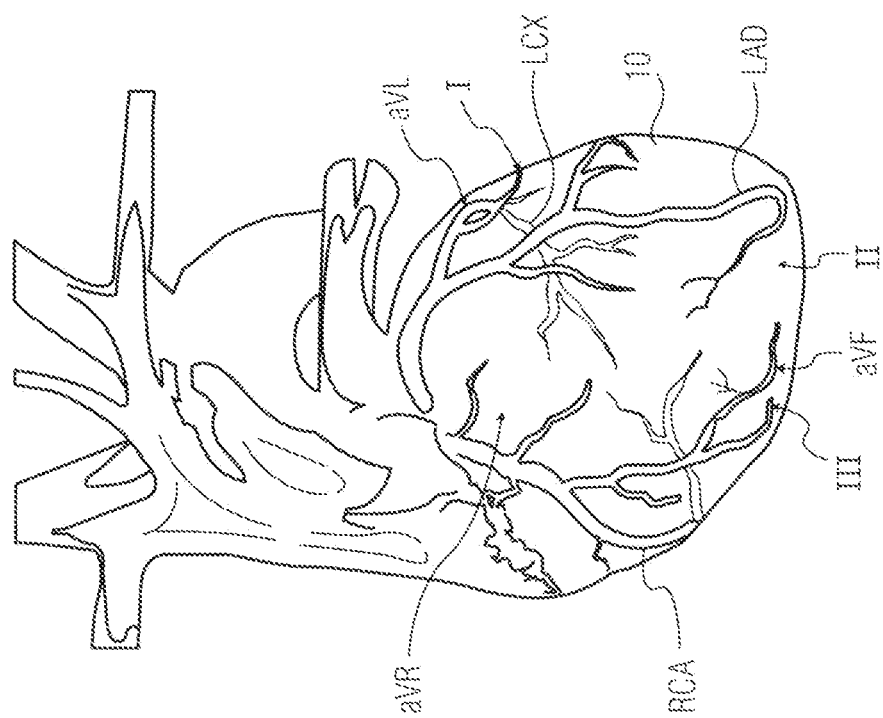

This principle may be further understood by relating the ECG leads to the anatomy of the coronary arteries as illustrated in FIGS. 11a and 11b. FIGS. 11a and 11b are anterior views of the heart 10 with the RCA, LCA, LCx, and LAD indicated as in FIG. 3. The pathways of the vessels are related to the three limb electrodes which, together with the vG electrode, are combined as shown above to produce the six limb leads I, II, III, aVR, aVL and aVF of a 12-lead system. The inferior leads II, III and aVF view the heart's electrical activity from the vantage point of the inferior or diaphragmatic wall of the left ventricle. The lateral leads I, aVL, V5 (shown as 5 in FIG. 11b) and V6 (shown as 6 in FIG. 11b) view electrical activity from the vantage point of the lateral wall of the left ventricle. The V1 and V2 leads (shown as 1 and 2 in FIG. 11b), derived from the electrodes on either side of the sternum (see FIG. 4a), view electrical activity from the vantage point of the septal wall of the heart. The anterior leads V3 and V4 view electrical activity from the vantage point of the anterior wall of the heart. The present invention takes into account the lead signals and their respective vantage points to the heart to identify a stenotic coronary artery.

FIG. 11c shows the positioning of ECG traces for the different leads typically used for an ECG report. Twelve-lead reports typically arrange the lead signals in a three by four matrix as shown by the first four columns in FIG. 11c. The signals of the inferior electrodes II, III, and aVF are located in the first and second columns, the lateral lead signals are positioned at the top of the first column (I), the middle of the second column (aVL), and in the fourth column (V5 and V6), and so forth. An embodiment of the present invention can advantageously use this standard orientation of the leads to perform its analysis and present the results to the clinician. In the example of FIG. 11c, a fifth column is added for higher order leads as shown in the following examples.

Figure 12B:
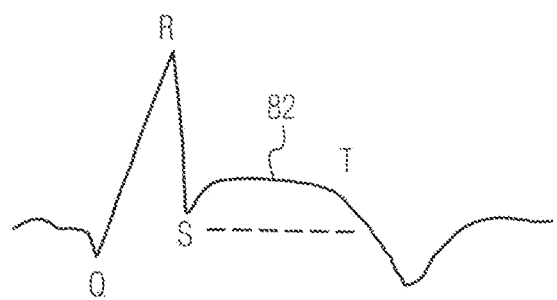
FIGS. 12b-12e illustrate ECG traces with elevated ST segments which may be used for culprit coronary artery identification in accordance with the principles of the present invention.
Figure 12C:
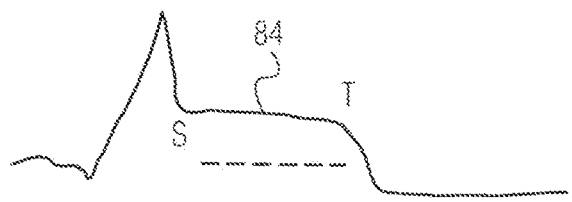
Figure 12D:
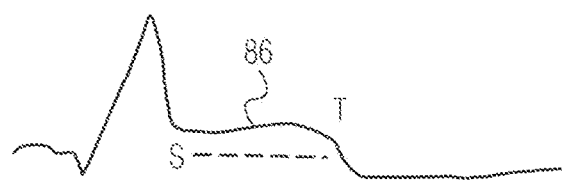
Figure 12E:
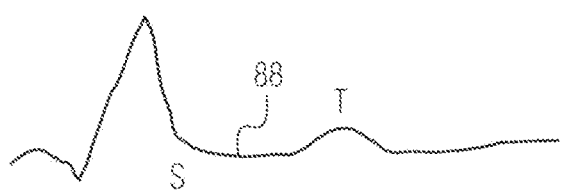

In accordance with a further aspect of the present invention, ECG lead signals are analyzed for particular patterns of elevated and depressed ST segments which relate to stenoses of specific coronary arteries and branch locations. In the normal ECG trace of FIG. 12a, the signal level of the ST segment 80 is at or very close to the nominal baseline of the ECG trace. When a coronary artery becomes fully occluded, the ST segment 82 for a lead in proximity to the artery will be highly elevated as shown in FIG. 12b, where the dashed line indicates the nominal baseline of the trace. The ST segment can be elevated 100 μvolts or more. ECG leads proximate to the other side of the heart will exhibit a corresponding depression, which can be detected and correlated with the elevated trace for positive identification of the ST elevation. Furthermore, the amount of ST elevation will vary as a function of the time and degree of stenosis. For example, shortly after the time of the event causing the obstruction, the ST segment of a lead will exhibit a relatively significant elevation 84 as shown in FIG. 12c. With the passage of time the elevation will decrease, and the ST elevation 86 can appear as shown in FIG. 12d. After a substantial period of time, as the heart begins adapting to its new physiological condition, or when an artery is only partially occluded, the ST segment will be only slightly elevated as shown at 88 in FIG. 12e. Thus, by querying the patient as to the time of onset of the chest pain the time of the event can be noted and the expected degree of elevation assessed. The degree of elevation can also be used to recognize only partially occluded vessels such as those in which an old blood clot has calcified over time. These indications can be used to set aside vessels not needing immediate attention while the interventional procedure is directed to the vessel which has just suffered major obstruction.

FIGS. 13a, 14a and 15a show examples of ECG reports in which the culprit coronary artery is identified for the clinician. In FIG. 13a the 12-lead traces are arranged in the 3×4 pattern described above. Also shown are three additional leads, two on the right side of the torso (V4R and V5R) with two on the posterior side of the heart (V8 and V9). The circled lead traces exhibit significant ST segment elevation in the anterior lead group of V3 and V4, as well as the adjacent leads V2 and V5. ST elevation is also seen in lateral leads V6, I and aVL. The presence of ST elevation in the lead group V2, V3, V4, V5 which may be accompanied by ST elevation in leads V6, I and aVL indicates obstruction of the left anterior descending (LAD) coronary artery, and this conclusion is seen to be printed and highlighted at the top of the report of FIG. 13a.

FIGS. 13b and 13c show why these anterior and lateral lead groups are indicative of LAD obstruction. FIG. 13b shows the lateral leads aVL and I viewing the left side of the heart and are thus more sensitive to left coronary symptoms than right coronary symptoms. Lead V6 of the lateral lead group is similarly oriented as shown in FIG. 13c. FIG. 13c also shows the anterior leads V3 and V4 in relation to the LAD as well as adjacent anterior leads V2 and V5. Since these leads view the anterior surface of the heart, they are more sensitive to LAD symptoms than LCx symptoms. If higher order lead sets are used instead of a 12-lead set, the ST elevated leads would be mirrored by ST depression in the leads facing the opposite wall of the heart. An example of this is seen in FIG. 13a, where the V4R lead viewing the right side of the heart exhibits some ST depression. Significant ST elevation in the two left side lead groups thus points to the LAD coronary artery as the culprit artery.

The ECG report of FIG. 14a shows ST elevation in inferior leads II, III and aVF. ST elevation is also present in posterior lead V8. The ST elevation of the posterior lead is mirrored by ST depression in anterior leads V1, V2 and V3. Furthermore, the level of ST depression of the anterior chest leads V1-V3 is greater than the ST elevation of the inferior limb leads II, III, and aVF. This set of measurements is indicative of obstruction of the left circumflex (LCx) coronary artery, as reported and highlighted at the top of the report of FIG. 14a. Adjacent posterior leads V7 and V9, when used, would show ST elevation similar to that of lead V8.

FIGS. 14b and 14c provide an anatomical illustration of this indication. The inferior leads II, III, and aVF, shown in FIG. 14b, view the heart from below and are thus less sensitive to symptoms of the superior portions of the left and right coronaries, and more sensitive to obstructions of the left circumflex as it wraps around and down the heart. The posterior leads V7, V8 and V9 oppose the posterior location of the LCx and are thus more sensitive to LCx symptoms than the more anterior RCA and LAD coronary arteries. The sensitivity of these posterior leads is mirrored by the ST depression of the anterior leads V1, V2 and V3. Thus, this set of ST elevation with matching ST depression is an indication of obstruction of the LCx coronary artery.

FIG. 15a shows an ECG report with ST elevation in the inferior lead group II, III, and aVF. The ST elevation in lead III is greater than that of lead II. ST elevation is also seen in right chest leads V4R and V5R. This set of measurements indicates right coronary artery (RCA) obstruction, as stated and highlighted in the ECG report. ST elevation of either the inferior lead group or the right chest lead group, or both, are indicative of RCA obstruction. ST elevation in lead aVR may also be present. Other indications which may also be present include possible ST depression in the anterior (V3, V4) and lateral (I, aVL, V5) lead groups, mirroring the ST elevation on the right side leads. Levels of ST depression are generally lower than the ST elevation in the inferior leads, as seen in FIG. 15a.

FIGS. 15b and 15c indicate the anatomical relationship of these indications. Inferior leads II, III, and aVF are sensitive to symptoms at the bottom of the heart where the RCA and LAD both supply blood, but the III lead is more proximate to the right side RCA than is the II lead proximate the LAD on the left side. The right chest leads including those shown in FIG. 15c are also more sensitive to right side symptoms. Also, the aVR lead is sensitive to symptoms in the region of the right ventricle and thus is also right side sensitive. ST depression mirroring this ST elevation would be expected in the anterior and lateral leads associated with the left side of the heart. It is therefore seen that this set of indications will identify the RCA as the culprit coronary artery.

Obstructions of the left main (LM) coronary artery, with its superior position at the top of the heart, may similarly be identified. Referring to the ECG report of FIG. 16, LM obstruction is indicated by ST elevation in the aVR lead with its association with an upper chamber (right ventricle) of the heart. This is at times accompanied by ST elevation in lead V1, however, in this case the V1 lead exhibits ST depression. Abnormal ST levels, to the extent present in other leads, will exhibit ST depression in most leads. In this case the circled traces of all of the other leads exhibit ST depression with the exception of lead V4R due to its proximity to lead aVR on the right side of the heart. The slight ST elevation of the V4R lead mirrors the ST depression seen in leads of the other side of the heart. This set of measurements indicates the LM is the culprit coronary artery. The typical diffuse ST depression seen in LM obstruction is not ordinarily recognized as an acute ischemic event but has the same or worse significance as other acute ischemic events.

In accordance with a further aspect of the present invention, certain ECG lead measurements and patterns are known to be related to occlusions in certain arterial locations. For instance, the ST-segment deviation pattern for proximal LAD occlusion is predominant ST elevation in the precordial leads with ST depression in leads III and aVF. ST elevation in leads III and aVF indicates a non-proximal location. The ST-segment pattern for proximal RCA occlusion is ST elevation in lead III greater than the ST elevation in lead II along with isoelectric or elevated ST in lead V1. From this a priori knowledge of relationships of ECG measurements and coronary occlusion locations a set of ECG measurements which have been useful to classify the culprit coronary artery and occlusion location within the artery are developed, including the ratio of ST elevation in lead II to the ST elevation in lead III; the ratio of ST depression in lead aVR to the ST depression in lead aVL; ST deviation in lead V1; ST axis, frontal plane; ST axis, horizontal plane (chest leads); inferior lead ST elevation and depression; anterior lead ST elevation and depression; and lateral lead ST elevation and depression. A classifier is then developed for ECG measurements which uses statistical methods of the possibility of strong association with different occlusion locations. For example a classifier has been developed to separate the likelihood of proximal RCA occlusion from mid/distal RCA and LCx occlusions. This specific implementation uses a logistic regression classifier using two ECG measurements called "STelevL2L3" (ST elevation in lead II minus ST elevation in lead III) and "trVcgSTangle" (vector-cardiogram transverse plane ST angle). The classifier is used to produce probability surfaces of the likelihood of the different arterial occlusion locations.

In the production of the probability surfaces, these ECG measurements are calculated for each ECG by the measurement processor 54 of FIG. 7, as illustrated in FIG. 9a. Two such measurements result in a single point on the contour plots. The value of the probability surface at that point gives the probability that the ECG belongs to that class. Each ECG will therefore have a probability that it is a member of each classification. The highest probability determines which class is most likely.

For example, suppose that an ECG has an ST axis value of 120 degrees and ST elev. II minus ST elev. III equal to −100. Accessing the probability surface plots with the point (−120, −100) will find the corresponding probabilities. In the illustrated example, the probability of non-proximal RCA is 0.6. The probability of proximal RCA is 0.4 and the probability of LCx is below 0.1. In this case the classifier output is that the location of the occlusion is the non-proximal RCA.

Partial occlusion of the proximal LAD can also be detected by ECG patterns in non-ST elevation MI (NSTEMI). NSTEMI is defined as acute MI by a biomarker that does not show diagnostic ST elevation. Deeply inverted T-waves in chest leads V2 through V4 indicate either proximal LAD occlusion or less often cerebrovascular accident (CVA). An implementation of the present invention is also capable of automated detection of proximal LAD occlusion by interpretation of a combination of ECG measurements of both the ST-segment and the T-wave in NSTEMI. ECG criteria which may be used in such an implementation include two contiguous leads of V2, V3, and V4 which have a T-wave amplitude of less than 0.5 mV; cases with both ST depression and ST elevation are excluded; T-waves in leads V2-V4 must be symmetric; QTc is greater than 460 msec for females and 450 msec for males; the QRS duration is less than 130 msec; and cases with automated interpretation of myocardial infarction, bundle branch block, and ventricular hypertrophy are excluded. Automated T-wave symmetry measurement is based on the ratio of the maximum slope on ascending and descending global T-waves; the ratio of the ascending and descending secant line slope; and the ratio of the areas before and after the peak of the global T-wave. As mentioned above, deeply inverted T-waves in chest leads V2 through V4 indicate either proximal LAD occlusion or less often cerebrovascular accident (CVA).

When a patient presents with symptoms of a heart attack but the ECG measurements reveal no significant ST elevation in any lead, the leads should be evaluated for any of the instances of ST depression listed above. The presence of the ST depression indications characteristic of a specific obstruction without ST elevation indicate a partial blockage or impending complete obstruction of the subject coronary artery, and should be indicated to the treating interventional cardiologist for consideration with other indications found by the physician.

In addition to the ST elevation and depression characteristics described above, other ECG measurements such as amplitudes and durations of Q wave, R wave, T wave and interwave intervals such as QRS and QT may also be used as applicable in the identification of the culprit coronary artery. The use of higher order lead sets including 13- to 18-lead ECG systems and 64- and 128-lead ECG body surface maps can provide additional incremental information to enhance the accuracy of culprit coronary artery identification. For systems with fewer than 12 leads, additional lead signals can be derived to implement the technique of the present invention with potentially reduced accuracy.

The final output of an implementation of the present invention includes an indication of one of the following: proximal LAD, mid/distal LAD, proximal RCA, mid/distal RCA, or LCx occlusion. This output would most likely be part of the text output of the DXL resting 12-lead algorithm.

What is claimed is:

1. A method of identifying the location of an occlusion of a culprit coronary artery associated with an ischemic event by means of an n-lead ECG system comprising:
   receiving ECG signals of the n-leads;
   analyzing the ECG lead signals for ST elevation;
   calculating a plurality of ECG measurements which are useful in the classification of a culprit coronary artery and the location of its occlusion;
   using the ECG measurements to develop a classifier of the probability of the location of an occlusion in different coronary artery locations;
   operating the classifier to identify a location with the highest probability of an occlusion; and
   identifying to a user a specific coronary artery location which is likely to be the site of an occlusion.

2. The method of claim 1, wherein using the ECG measurements to develop a classifier further comprises producing contour plots of probability surfaces of the likelihood of occlusion in different coronary artery locations.

3. The method of claim 2, wherein the different coronary artery locations are non-proximal RCA, proximal RCA and LCx.

4. The method of claim 2, wherein operating the classifier further comprises:
   accessing the contour plots with ECG measurements to identify a probability value at each of a plurality of locations; and
   identifying a location from the contour plot with the highest probability value.

5. The method of claim 1, wherein developing a classifier further comprises developing a logistic regression classifier.

6. The method of claim 1, wherein the different coronary artery locations are proximal LAD and mid/distal LAD.

7. The method of claim 6, wherein analyzing further comprises analyzing the ECG lead signals for characteristics of NSTEMI.

8. The method of claim 7, wherein calculating further comprises calculating measurements of deeply inverted and symmetric T-waves.

9. The method of claim 1, further comprising:
   analyzing an ST elevation pattern for an indication of the obstruction of a specific coronary artery or branch; and
   identifying to a user a specific coronary artery or branch as a culprit coronary artery.

10. The method of claim 9, wherein analyzing the pattern of ST elevation further comprises identifying ST elevation in an anterior lead group including one or more of leads V2, V3, V4, V5 which may be accompanied by ST elevation in lateral lead group including one or more of leads V6, I, aVL as indicating the obstruction of the left anterior descending (LAD) coronary artery; and
   wherein identifying further comprises identifying the LAD coronary artery as a culprit coronary artery.

11. The method of claim 9, wherein analyzing the pattern of ST elevation further comprises identifying ST elevation in inferior lead group including one or more of leads II, III, aVF and in posterior lead group including one or more of leads V7, V8, V9; and
   analyzing the traces of anterior lead group including one or more of leads V1, V2, V3 for ST depression and identifying ST depression in the lead group;
   wherein identifying further comprises identifying the left circumflex (LCx) coronary artery as a culprit coronary artery.

12. The method of claim 9, wherein analyzing the pattern of ST elevation further comprises identifying ST elevation in inferior lead group including one or more of leads II, III, aVF and/or in right chest leads including one or more of leads V3R-V5R, wherein the level of ST elevation in lead III is greater than the level of ST elevation in lead II; and
   wherein identifying further comprises identifying the right coronary artery (RCA) as a culprit coronary artery.

13. The method of claim 9, wherein analyzing the pattern of ST elevation further comprises identifying ST elevation in lead aVR; and
   further comprising identifying ST depression in a plurality of other leads; and
   wherein identifying further comprises identifying the left main (LM) coronary artery as a culprit coronary artery.

14. The method of claim 1, wherein n is twelve.

* * * * *